(12) United States Patent
Sickenberger et al.

(10) Patent No.: US 6,967,338 B1
(45) Date of Patent: Nov. 22, 2005

(54) MICRO UV PARTICLE DETECTOR

(75) Inventors: David W. Sickenberger, Bel Air, MD (US); Richard D. Sickenberger, Daytona Beach, FL (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 43 days.

(21) Appl. No.: 10/720,877

(22) Filed: Nov. 24, 2003

Related U.S. Application Data

(60) Provisional application No. 60/428,824, filed on Nov. 25, 2002.

(51) Int. Cl.[7] ............................................. G01N 24/61
(52) U.S. Cl. ................................................. 250/461.1
(58) Field of Search ........................... 250/461.1, 458.1

(56) References Cited

U.S. PATENT DOCUMENTS

| | | | | |
|---|---|---|---|---|
| 4,286,876 A | * | 9/1981 | Hogg et al. ................. 356/343 |
| 5,675,155 A | * | 10/1997 | Pentoney et al. ......... 250/458.1 |
| 5,946,091 A | * | 8/1999 | Yufa ........................... 356/336 |
| 6,120,166 A | * | 9/2000 | Price ........................... 362/302 |
| 6,594,009 B2 | * | 7/2003 | Saccomanno ............... 356/246 |

* cited by examiner

*Primary Examiner*—David Porta
*Assistant Examiner*—Marcus Taningco
(74) *Attorney, Agent, or Firm*—Ulysses John Biffoni

(57) ABSTRACT

The invention provides particle detectors and detection methods. A particle detector includes a spherical/ellipsoid shell comprising spherical and ellipsoid mirrors that define a focal point within an interior of the shell, a pair of opposing tubes passing through the spherical/ellipsoid shell and directed at the focal point for directing particles to the focal point, and a light source directed at the focal point for directing light at the particles to generate fluorescence from the particles at or near the focal point.

28 Claims, 9 Drawing Sheets

MICRO UV PARTICLE DETECTOR

CROSS REFERENCE TO RELATED APPLICATIONS

This application claims priority to U.S. Provisional Patent Application Ser. No. 60/428,824 filed Nov. 25, 2002 and titled "MICRO UV DETECTOR," which application is commonly assigned and incorporated by reference herein.

STATEMENT OF GOVERNMENT INTEREST

The invention described herein may be manufactured and used by or for the Government of the United States of America for governmental purposes without the payment of any royalties thereon or therefor.

TECHNICAL FIELD OF THE INVENTION

The present invention relates generally to particle detectors and, in particular, to micro UV detectors.

BACKGROUND OF THE INVENTION

It is well known that biological materials fluoresce when irradiated with light in the ultraviolet region. In general, the excitation light has a wavelength from about 260 to 360 nm. The emission from the biological materials can be anywhere from the excitation wavelength (scattered) to the visible range. Many particle detectors for detecting biological agent aerosols, e.g., the Tier-3 Biological Aerosol Warning System, are based on this phenomenon.

Historically, these particle detectors use a laser for the excitation process. One or more photon detectors, or photo multipliers, are used to capture emission from the sample particles and scattering. Many particle detectors also employ a flow-through design, where the sampled particles pass through the excitation light at a relatively fast pace. This is done to improve the sampling statistics. However, these particle detectors are often undesirably large, heavy, and expensive and consume undesirable amounts of power for many applications, such as field applications, e.g., particle detectors for use with military ground forces, on moving ground and air platforms, within structures, etc.

For the reasons stated above, and for other reasons stated below which will become apparent to those skilled in the art upon reading and understanding the present specification, there is a need in the art for alternative particle detectors for detecting biological agent aerosols.

SUMMARY

The above-mentioned problems with particle detectors for detecting biological agent aerosols and other problems are addressed by the present invention and will be understood by reading and studying the following specification.

Embodiments of the present invention provide particle detectors capable of detecting biological agent aerosols. The particle detectors direct opposing flows into a beam of ultra-violet light to generate fluorescence from the particles. The opposing flows act to reduce to the particle velocities within the light, thus increasing the residence time of the particles within the light.

For one embodiment of the present invention, a particle detector includes a spherical/ellipsoid shell comprising spherical and ellipsoid mirrors that define a focal point within an interior of the shell, a pair of opposing tubes passing through the spherical/ellipsoid shell and directed at the focal point for directing particles to the focal point, and a light source directed at the focal point for directing light at the particles to generate fluorescence from the particles at or near the focal point.

For another embodiment, a method for detecting particles includes directing a pair of opposing particle flows at a focal point within a spherical/ellipsoid cavity having an ellipsoid mirror and a spherical mirror, directing ultra-violet light at the focal point to illuminate the particles at or near the focal point to generate fluorescence from the particles at or near the focal point, and directing fluorescence generated at or near the focal point to a target point.

Further embodiments of the invention include methods and apparatus of varying scope.

BRIEF DESCRIPTION OF THE DRAWINGS

FIG. 1 is a perspective view illustrating a particle detector according to an embodiment of the present invention.

FIG. 2 is an exploded view of the detector of FIG. 1.

FIG. 3 illustrates a light emitter according to another embodiment of the present invention.

FIG. 4 is a perspective cutaway view of a spherical/ellipsoid shell of a particle detector according to another embodiment of the present invention.

FIG. 5 is a view taken along line V—V of FIG. 4.

FIG. 6 illustrates a particle detector connected to a pump according to another embodiment of the present invention.

FIG. 7 is a view taken along line VII—VII of FIG. 4 according to another embodiment of the present invention.

FIG. 8 illustrates a particle detector having an external light source according to another embodiment of the present invention.

FIG. 9 is a cross-sectional view of a concentric-tube arrangement according to another embodiment of the present invention.

DETAILED DESCRIPTION

In the following detailed description of the invention, reference is made to the accompanying drawings that form a part hereof, and in which is shown, by way of illustration, specific embodiments in which the invention may be practiced. In the drawings, like numerals describe substantially similar components throughout the several views. These embodiments are described in sufficient detail to enable those skilled in the art to practice the invention. Other embodiments may be utilized and structural, logical, and electrical changes may be made without departing from the scope of the present invention. The following detailed description is, therefore, not to be taken in a limiting sense, and the scope of the present invention is defined only by the appended claims and equivalents thereof.

FIG. 1 illustrates a mini UV particle detector 1 according to an embodiment of the present invention. FIG. 2 is an exploded view of detector 1 when viewed from an angle. Sample flow tubes 2 are inserted into opposing holes 38, one of which is shown in FIGS. 1 and 2, of an end cap 3 (shown in FIGS. 1 and 2) of detector 1. For one embodiment, sample flow tubes 2 are of a rigid material, such as aluminum, and are substantially non-fluorescent. For another embodiment, each of sample flow tubes 2 is coated with an enhanced aluminum coating to reflect any fluorescent light generated within detector 1. Enhanced aluminum coatings are mirror coatings created by coating aluminum with a multi-layer dielectric film. Enhanced aluminum coatings are well known in the art and will not be discussed further here. End cap 3 can be of any rigid material, such as plastic or metal.

Figure 1:
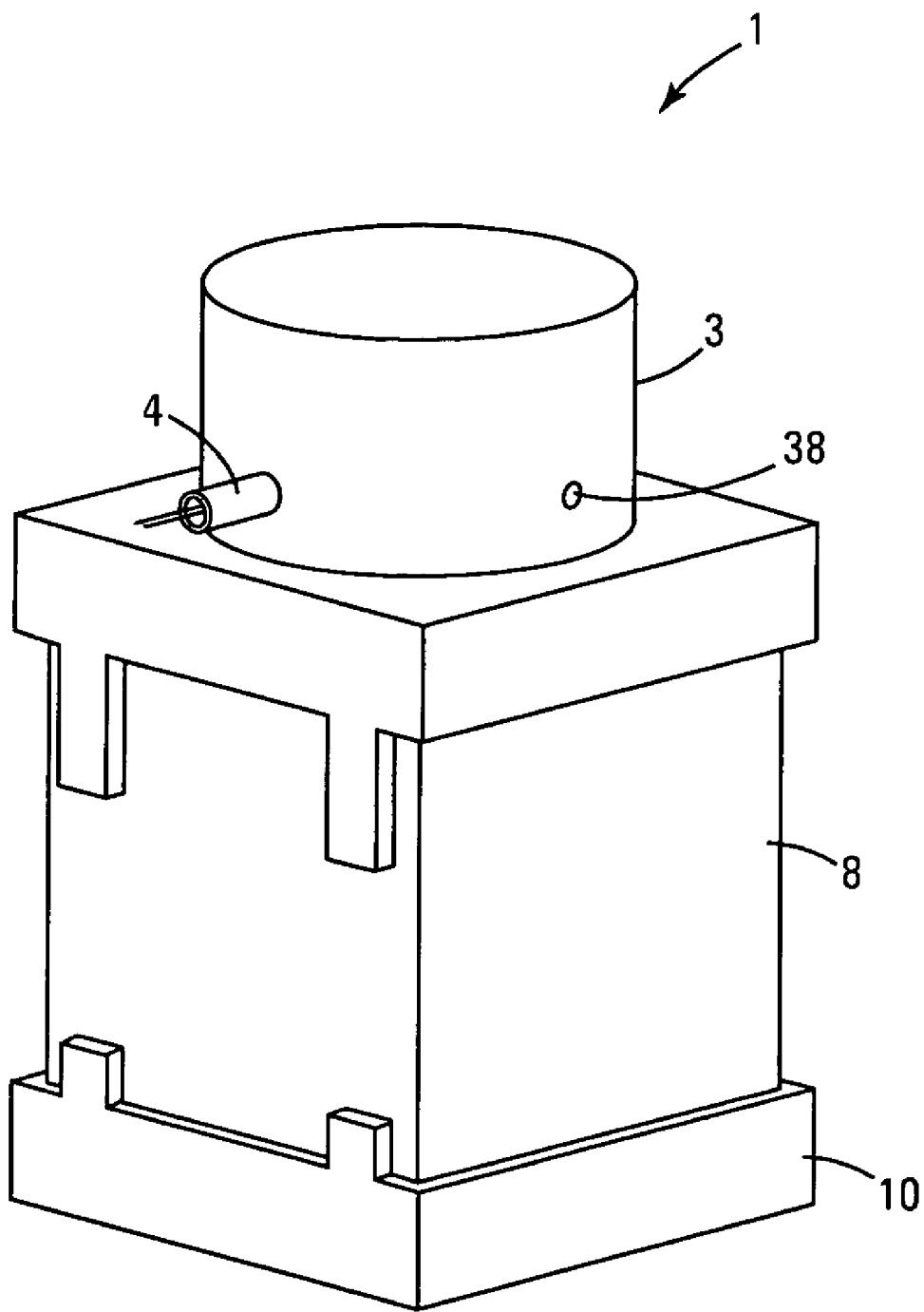

A light emitter 4 (shown in FIGS. 1 and 2) inserts into a hole 40 (shown in FIG. 2) in end cap 3. An ellipsoid mirror 5 is disposed within end cap 3. For one embodiment, ellipsoid mirror 5 has holes 14 and 15 (shown in FIG. 2) that respectively align with holes 40 and 38 of end cap 3 for respectively receiving sample tubes 2 and emitter 4. Ellipsoid mirror 5 is discussed in more detail below. A spherical mirror 6 and a filter 7 insert into a recess 42 in a body 8 (shown in FIGS. 1 and 2) of detector 1. Spherical mirror 6 is discussed in more detail below.

Filter 7 can be any standard, commercially available glass filter that is capable of removing the same frequency light emitted by the light emitter 4. Filter 7 may be coated with a reflective or adsorbing coating that acts to substantially prevent fluorescence from the glass. Filter 7 will, however, allow longer wavelength light to pass through it. For one embodiment, cut off frequencies of filter 7 are 350–400 nm. Brysen Optical Corporation (Florida, USA) manufactures a suitable filter.

Body 8 can be of any rigid material such as plastic, metal, or the like. Body 8 has a recess (not shown) opposite recess 42 (e.g., at the bottom of body 8) to receive a photon counter 9. A Hamamatsu H7467 manufactured by Hamamatsu Photonics K.K. (Hamamatsu, J P) is a suitable photon counter. Photon counter 9 counts photons passing through filter 7 and thus measures the total fluorescence signal produced within detector 1. Photon counter 9 is held in place by an end cap 10 (shown in FIGS. 1 and 2) of detector 1 located opposite end cap 3. Detector 1 is secured with mounting hardware 11.

Figure 3:
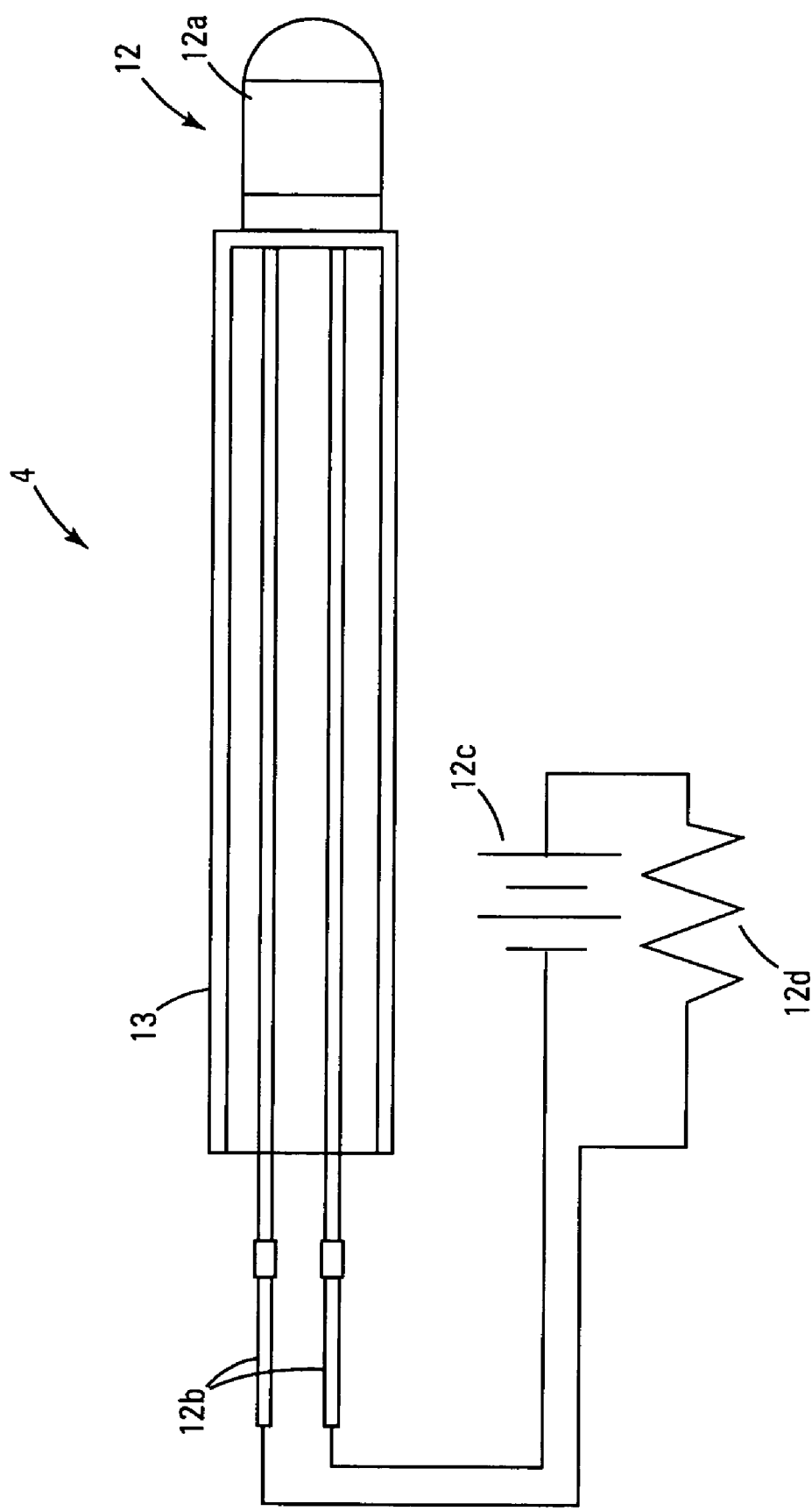

FIG. 3 illustrates light emitter 4 for an embodiment of the present invention. For one embodiment, light emitter 4 includes an ultra-violet light emitting diode (UV-LED) 12 mounted in a holder 13. LED 12 may be coated to insure that only desired wavelengths of light are emitted. For another embodiment, LED 12 has a UV LED light source 12a and two wire leads 12b for delivering power to LED light source 12a. LED 12 is powered by a power supply or battery 12c. A resistor 12d controls the current through LED 12. Holder 13 can be of a rigid and non-fluorescent material, such as aluminum. Holder 13 supports LED 12 inside of end cap 3 and ellipsoid mirror 5. For some embodiments, the LED 12 requires only a modest amount of power, typically milliwatts, and delivers almost 1 milliwatt of UV power at a wavelength of around 350 nm. Alternatively, small UV lasers are suitable light sources.

Figure 4:
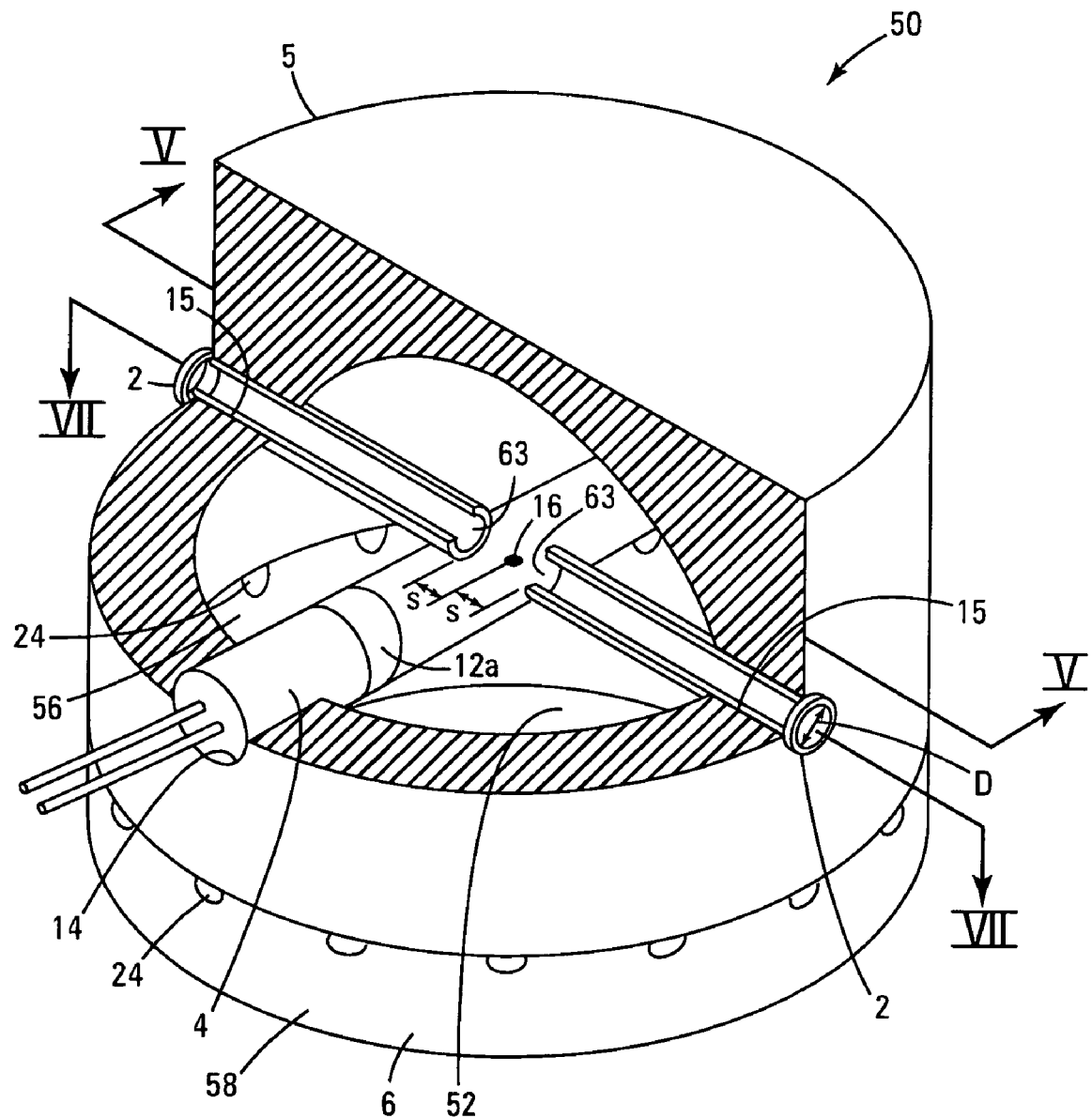
Figure 5:
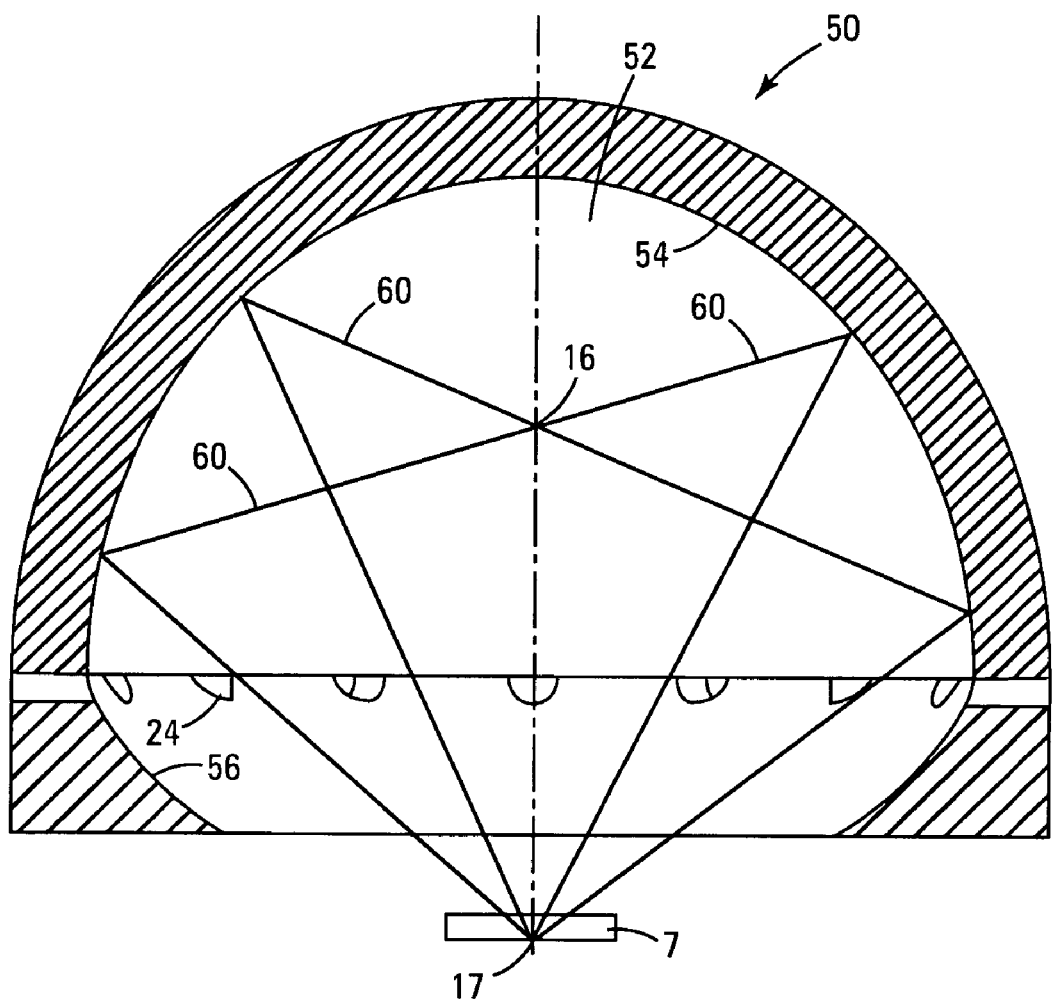

When detector 1 is assembled, ellipsoid mirror 5 abuts spherical mirror 6 to form a spherical/ellipsoid shell 50 of detector 1, as shown in FIGS. 4 and 5 for another embodiment of the present invention. FIG. 4 is a perspective cutaway view, and FIG. 5 is a view taken along line V—V of FIG. 4. An interior of spherical/ellipsoid shell 50 defines a spherical/ellipsoid cavity 52 within detector 1, as shown in FIGS. 4 and 5. FIG. 4 shows emitter 4 passing radially through hole 14 of ellipsoid mirror 5 so that LED light source 12a is located within spherical/ellipsoid cavity 52. FIG. 4 also shows sample tubes 2 passing radially through holes 15 of ellipsoid mirror 5 into spherical/ellipsoid cavity 52 so that sample tubes 2 are positioned opposite one another.

Ellipsoid mirror 5 can be fabricated out of any rigid material, such as aluminum. An interior surface 54 (shown in FIG. 5) of ellipsoid mirror 5 is reflective to ultra-violet light. For one embodiment, interior surface 54 is coated with an enhanced aluminum coating that for another embodiment has maximum reflective properties for wavelengths between about 350–700 nm. Spherical mirror 6 can be fabricated out of any rigid material, such as aluminum. An interior surface 56 (shown in FIGS. 4 and 5) of spherical mirror 6 is reflective to ultra-violet light. For one embodiment, interior surface 56 is coated with an enhanced aluminum coating that for another embodiment has maximum reflective properties for wavelengths between about 350–700 nm. For some embodiments, notches 24 (shown in FIGS. 1, 4, and 5) are disposed in spherical mirror 6. Notches 24 extend radially between and pass through the interior surface 56 and an outer surface 58 of spherical mirror 6, and thus extend radially from spherical/ellipsoid cavity 52 to an exterior of spherical/ellipsoid shell 50, as shown in FIG. 4.

Surfaces 54 and 56 of spherical/ellipsoid cavity 52 define a focal point 16 within spherical/ellipsoid cavity 52, as shown in FIGS. 4 and 5. Any light emitted at or near focal point 16 is directed to a target point 17 located, for one embodiment, outside of spherical/ellipsoid cavity 52, e.g., below spherical mirror 6, as shown in FIG. 5. This is illustrated by ray traces 60, for another embodiment, in FIG. 5. Substantially all of the light at or near focal point 16 that does not irradiate target point 17 directly is reflected off of the ellipsoid mirror 5 and spherical mirror 6 and is focused on target point 17.

The excitation energy from light source 12a is also directed at focal point 16, as shown in FIG. 4. This can be accomplished by focusing the light from light source 12a using lenses (not shown), directing it using fiber optics (not shown), or by physically placing LED light source 12a at or near focal point 16. For another embodiment, light source 12a is replaced with a laser-based UV light source that is mounted so its beam hits focal point 16.

Prior to hitting target point 17, the light emitted at or near the focal point 16 passes through the filter 7 installed below the spherical mirror 6, as shown in FIG. 5. Filter 7 removes selected wavelengths of light. For one embodiment, filter 7 removes the excitation wavelength produced by a light source, such as light source 12a or the laser, while allowing longer wavelengths between about 350 and 700 nm to pass. The light passed through filter 7, and the filtered light is directed from filter 7 through target point 17 to the photon counter 9. Photon counter 9 measures any light, specifically fluorescence, produced at focal point 16. This can also be accomplished using other light-measuring devices, such as a photomultiplier. For one embodiment, photon counter 9 counts the number of photons during a period of time to determine the intensity of the fluorescence signal. For another embodiment, photon counter 9 outputs the intensity is a digital value.

Figure 2:
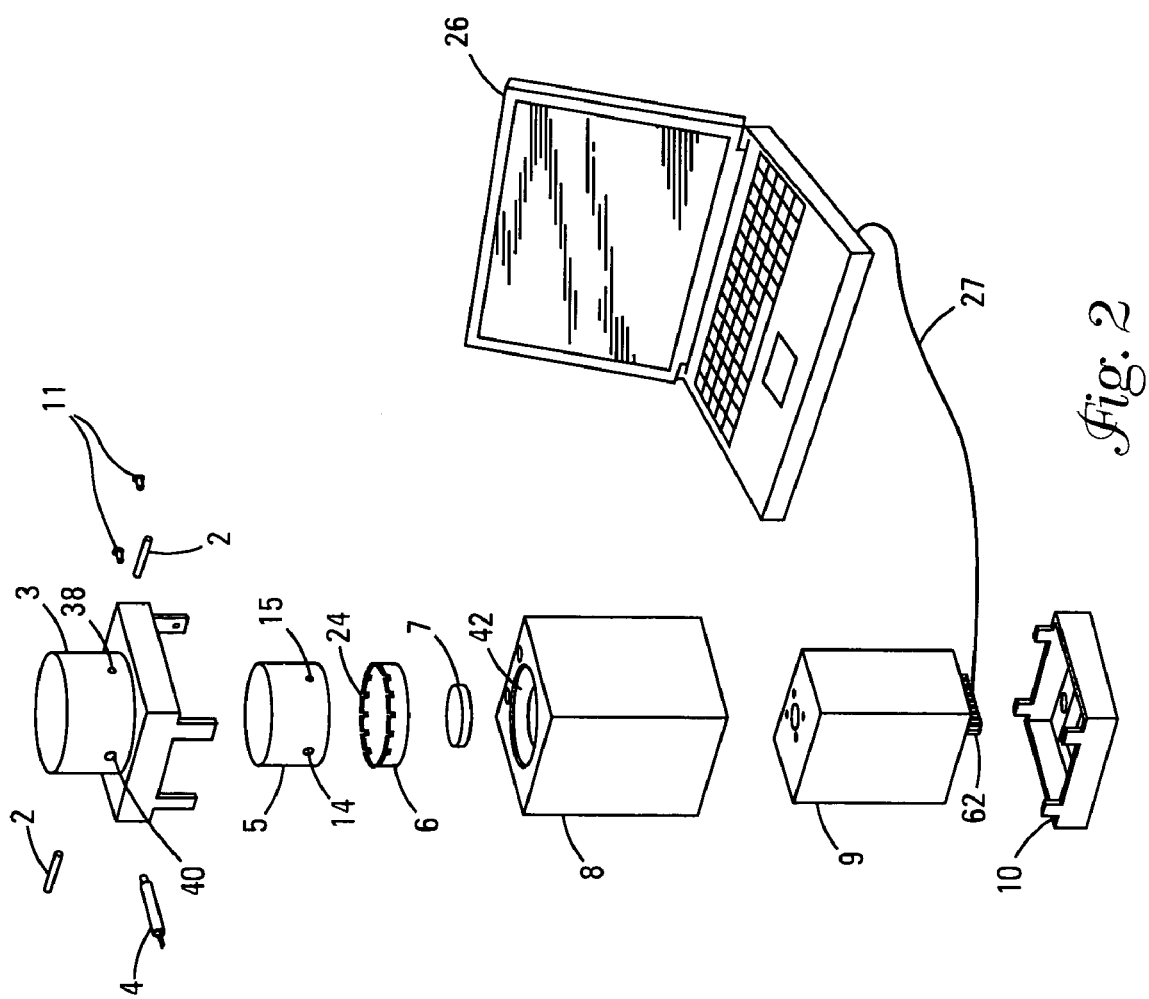

The detected photons counted by the photon counter 9 are transmitted to a data processor of a computer 26, as shown in FIG. 2. For one embodiment, an interface 62, such as an RS232 interface of photon counter 9, connects photon counter 9 to computer 26 via a line 27. The computer controls the counter's integration time and records the actual counts. Software within the computer determines if preset alarm thresholds are exceeded. In such a case, the computer would generate appropriate warning messages. Alternatively, a dedicated microprocessor could fulfill this role.

The focal point 16 is also used for the collection of aerosol particles (particles contained within a gas flow, such as air). Directing sample flow tubes 2 at focal point 16, as shown in FIG. 4, and directing the aerosol particles through sample flow tubes 2 into spherical/ellipsoid cavity 52 so that the particles exit the tubes and travel toward focal point 16 accomplishes this. Placing sample flow tubes 2 in opposition to one another, as shown in FIG. 4, acts to cause particles exiting one tube to be influenced by the flow from the opposing tube. This acts to reduce the velocity (or inertia) of the particles at focal point 16 that produces a stalling effect, thereby increasing the residence time of the particles at focal point 16 and thus the residence time of the particles within the excitation beam produced by the light source. For another embodiment, the flow in the respective sample flow tubes is substantially balanced. This acts to further increase the residence times. For other embodiments, exits 63 of sample tubes 2 are substantially equidistant from focal point 16, and/or their inside diameters D (shown in FIG. 4) are substantially equal.

For various embodiments, the stalled effect depends on a distance S (shown in FIG. 4) between an exit 63 of each of the sample flow tubes 2 and the focal point 16, the inside diameter D of the sample flow tubes 2, and a flow rate through the sample flow tubes 2. For example, the residence time of the particles within the excitation beam is increased by about a factor of 100 compared to flow-through detectors without opposing flows for two sample tubes, each having an inside diameter D of about 2 mm, each located at a distance S of about 2 mm from focal point 16, and each having a flow rate of about 1 liter/minute therethrough.

Increasing the residence time of the particles within the excitation beam acts to increase the sensitivity of detector 1 compared to flow-through detectors without opposing flows. Moreover, it acts to reduce the power requirements of detector 1 compared to flow-through detectors without opposing flows. Increasing the residence time of the particles within the excitation beam also acts to increase the total number of photons that interact with the particle and those emitted as fluorescence.

The air and particles are exhausted from spherical/ellipsoid cavity 52 through notches 24 in spherical mirror 6. For various embodiments, notches 24 distribute the flow so that the flow does not form eddies and turbulent streams.

Figure 6:
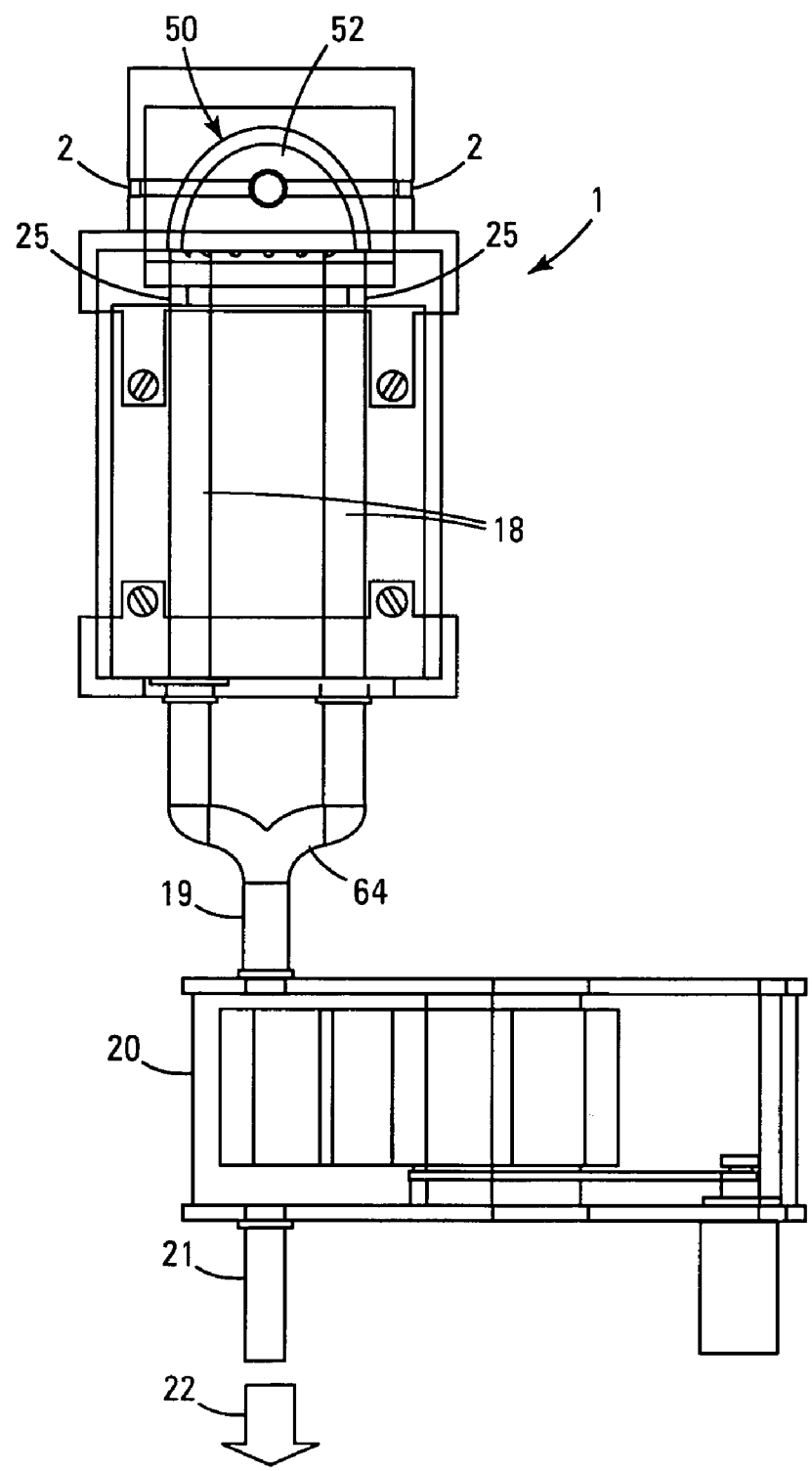

FIG. 6 illustrates an external pump 20 connected to detector 1 according to another embodiment of the present invention. Pump 20 creates a suction at inlets to sample tubes 2 that draws ambient air, e.g., containing particles, such as of biological materials, through sample tubes 2, into spherical/ellipsoid cavity 52, and out through notches 24, as described above. After exiting notches 24, the air is directed through internal conduits 25 and 18 (shown in FIG. 6) of detector 1 and then exits detector 1. For one embodiment, the air is directed through a single conduit 19 after exiting detector 1 via a flow combining fitting 64, such as a tee or the like. Specifically, internal conduits 25 are fluidly coupled between notches 24 and internal conduits 18. Notches 24 and internal conduits 25 and 18 fluidly couple spherical/ellipsoid cavity 52 to pump 20, as shown in FIG. 6.

For one embodiment, the flows through internal conduits 18 are combined within detector 1 and exit detector 1 as a single flow. Using two internal conduits 18 acts to reduce or prevent turbulence in the flow through notches 24 in spherical mirror 6. Pump 20 exhausts the flow through an exhaust port 21. An arrow 22 in FIG. 6 indicates the exhausted flow.

Figure 7:
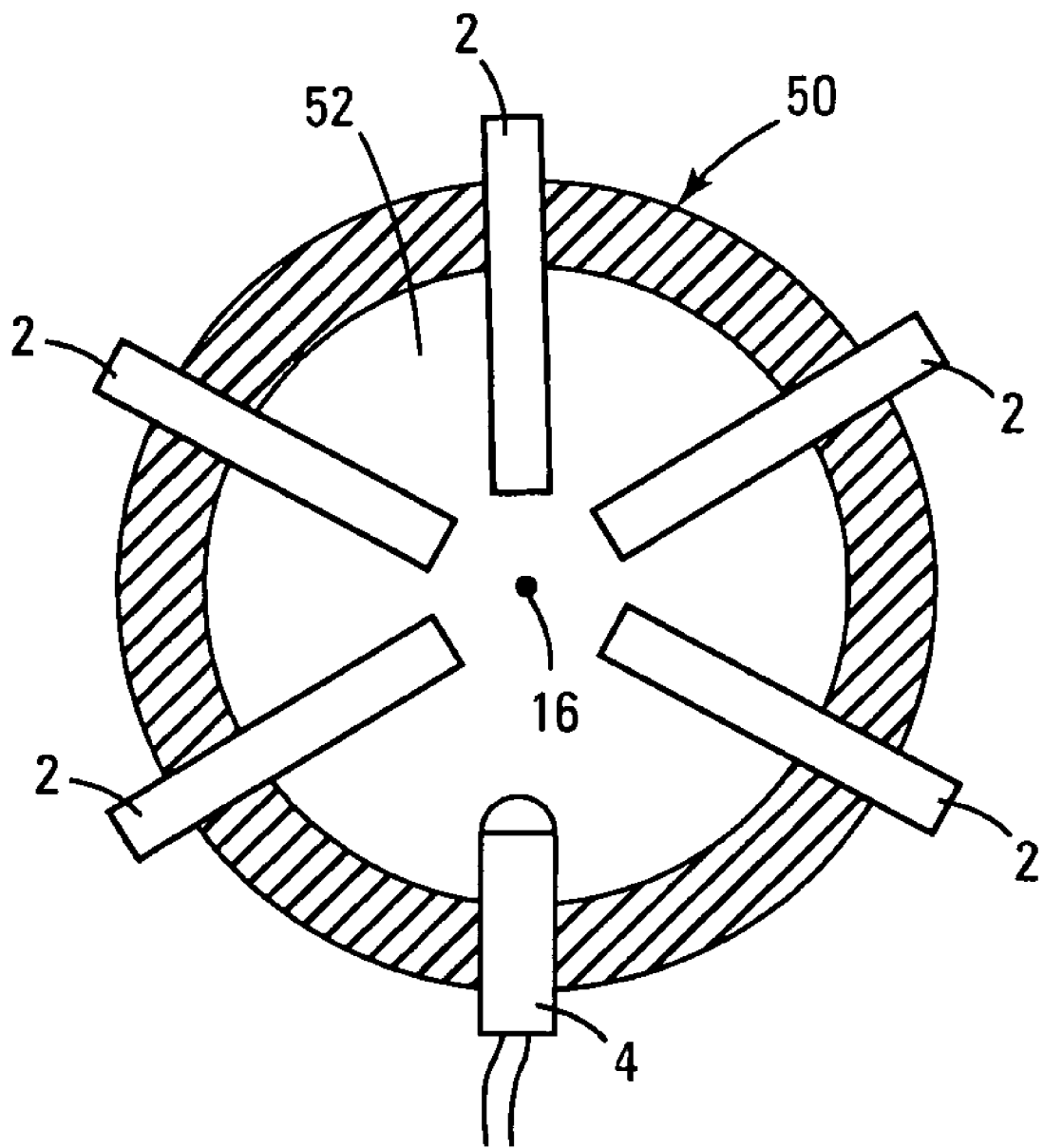

FIG. 7 is a cross-section of spherical/ellipsoid shell 50 viewed along line VII—VII of FIG. 4 according to another embodiment of the present invention. FIG. 7 illustrates two pairs of opposing sample tubes 2 directed at the focal point 16.

For various embodiments, filter 7 is used to remove the wavelength emitted from the light source due to scatter off of the sample particles. For some embodiments, the scattered light is detected using an independent photo detector (not shown), such as a photodiode mounted elsewhere within spherical/ellipsoid cavity 52 to measure the scatter component.

In operation, pump 20 is attached to detector 1, as shown in FIG. 6. As result, ambient air containing particles, e.g., of biological materials, is drawn into the two (or four) sample flow tubes 2. The particles are directed through sample flow tubes 2 and, for some embodiments, reach a near-terminal velocity within the air stream as it accelerates within sample flow tubes 2. Upon exiting sample flow tubes 2, some of the particles, e.g., between about 2–10 microns, flow toward the opposing sample flow tube 2. As these particles get closer to the opposing tube, the opposing flows act to reduce the velocities of the particles at or near the focal point 16 to produce the stalling effect. The reduced particle velocities provide additional time for irradiation by light from the light source. These particles are then directed through the notches 24, into the internal channels 25 and 18, through pump 20, and are exhausted, as indicated by arrow 22. The bulk air component and smaller particles bend and flow to the notches 24 in the spherical mirror 6 after exiting sample flow tubes 2 without flowing to focal point 16. This flow is directed through the notches 24, into the internal channels 25 and 18, through pump 20, and is exhausted, as indicated by arrow 22.

The LED light source 12a is positioned near focal point 16 and is positioned so that its UV light illuminates the area at and around focal point 16 and thus the particles at or near focal point 16. In the case of particles of biological materials or other materials capable of fluorescing, the UV light generates fluorescence from the particles. Most of the fluorescence is directed toward surfaces 54 and 56 of spherical/ellipsoid shell 40, as shown in FIG. 5 by ray traces 60. Surfaces 54 and 56 reflect and focus the fluorescence. Any fluorescence hitting surface 54 of ellipsoid mirror 5 is reflected and focused to the target point 17 below spherical mirror. Any fluorescence hitting interior surface 56 of spherical mirror 6 is reflected back to the focal point 16 and onto surface 54. This reflected fluorescence is again reflected and focused by interior surface 54 back to the target point 17.

Fluorescence focused to the target point passes through filter 7. Filter 7 removes any scattered light from the irradiating light source and any other undesired wavelengths from the fluorescence and outputs fluorescence photons. The fluorescence photons are received at photon counter 9 that outputs an electrical signal indicative of the fluorescence. The electrical signal is sent to an external microprocessor or computer 26 for measuring the fluorescence. An alarm is generated when this signal exceeds a preset threshold.

Figure 8:
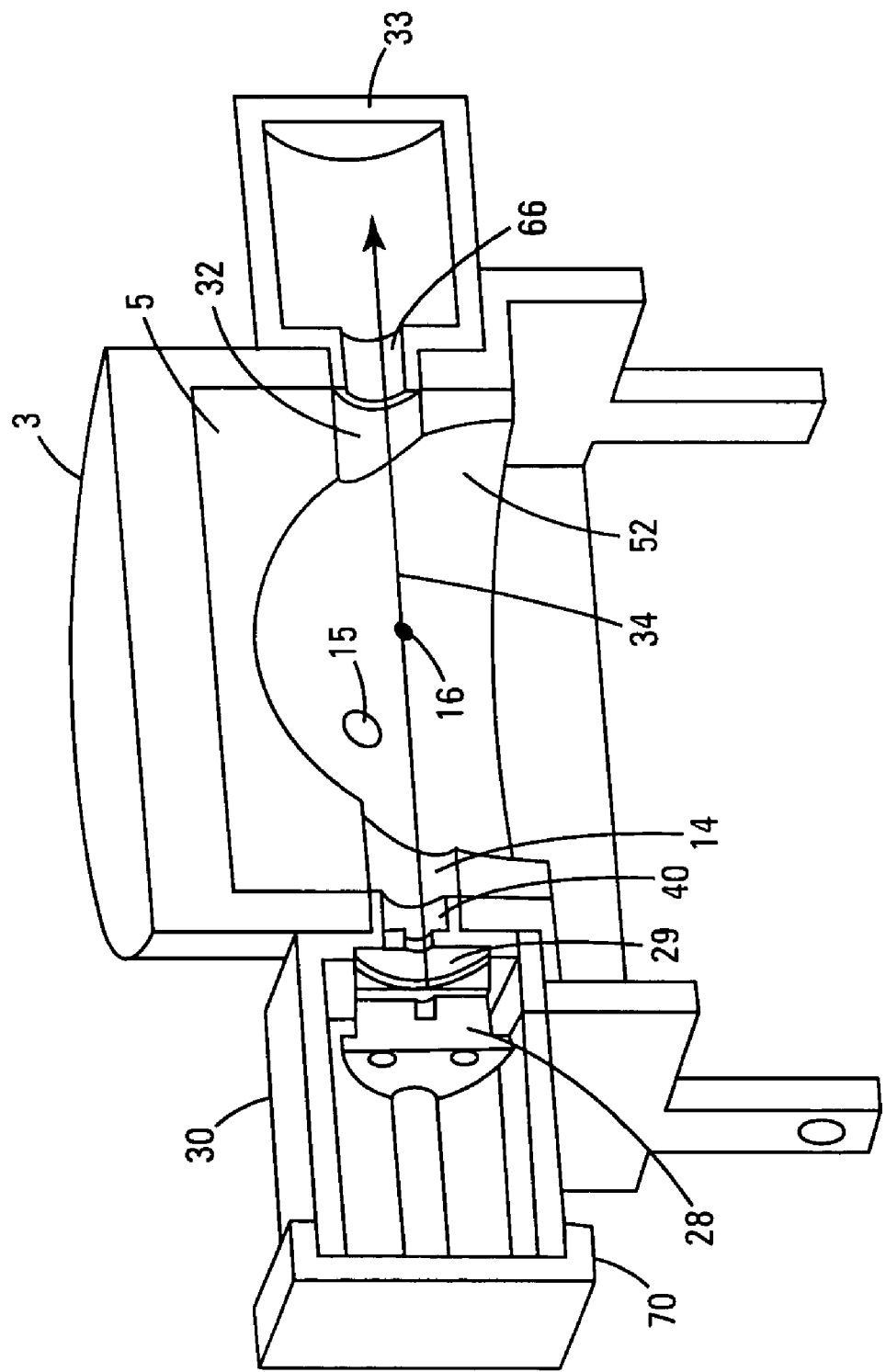

For another embodiment, emitter 4, and thus LED light source 12a, is replaced with an external ultra-violet light source 28, such as a UV laser, that is mounted externally of end cap 3 so its beam 34 hits focal point 16, as illustrated in FIG. 8 according to another embodiment of the present invention. For one embodiment, beam 34 is directed through an external filter 29 located externally of end cap 3, as shown in FIG. 8, for removing undesired wavelengths of light from light source 28. Beam 34 is then directed through the hole 40 in end cap 3 and through the hole 14 in ellipsoid mirror 5 that is aligned with hole 40 to access the focal point 16. Beam 34 is then directed through an outlet hole 32 in ellipsoid mirror 5 for exiting spherical/ellipsoid cavity 52, through an outlet 66 in end cap 3, and, for one embodiment, into an optical light dump 33 connected to an exterior of end cap 3. Light dump 33 acts to prevent light from beam 34 from being reflected back into spherical/ellipsoid cavity 52.

For another embodiment, a housing 30 connected to an exterior of end cap 3 and closed by a cover 70 contains light source 28 and external filter 29.

Figure 9:
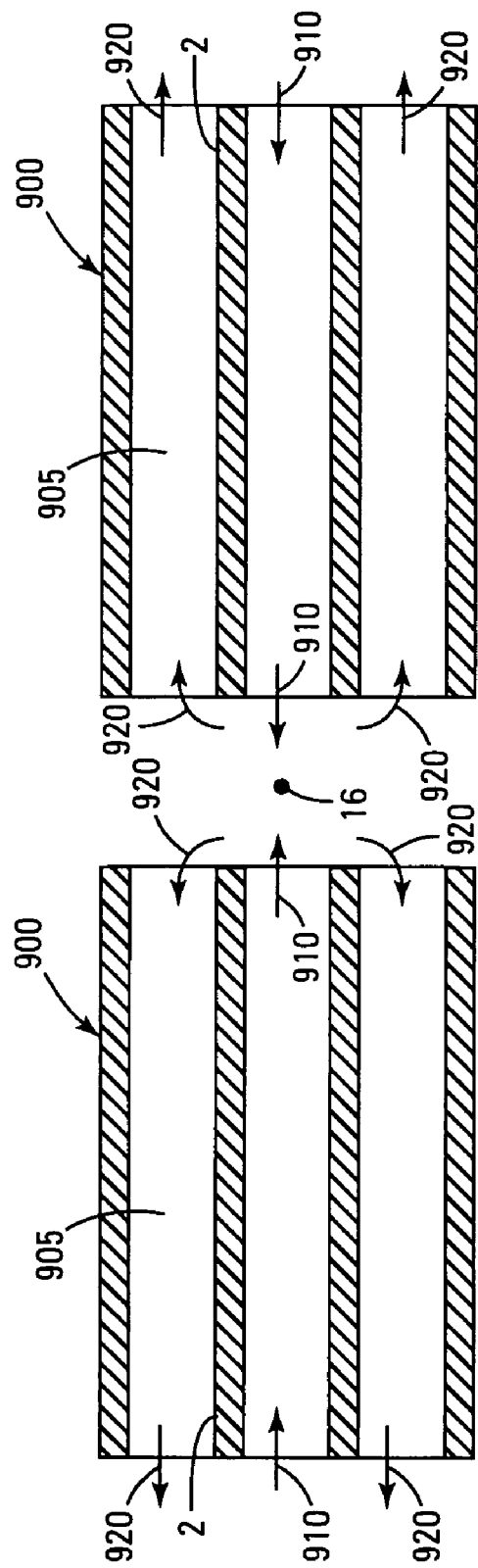

For one embodiment, each tube 2 passes substantially concentrically through a tube 900 to form a flow passage 905 between an exterior of tube 2 and an interior of tube 900, as shown in FIG. 9. Aerosol particles flow into spherical/ellipsoid cavity 52 through sample flow tubes 2 and travel toward focal point 16 after exiting sample flow tubes 2, as indicated by arrows 910 in FIG. 9. Instead of exhausting the air and particles from spherical/ellipsoid cavity 52 through the notches 24 in spherical mirror 6, as described above, the air and particles are exhausted from spherical/ellipsoid cavity 52 through flow passages 905, as indicated by arrows 920 and are subsequently directed to pump 20.

CONCLUSION

Embodiments of the present invention provide particle detectors capable of detecting biological agent aerosols. For one embodiment, a particle detector includes a spherical/ellipsoid shell comprising spherical and ellipsoid mirrors that define a focal point within an interior of the shell, a pair of opposing tubes passing through the spherical/ellipsoid shell and directed at the focal point for directing particles to the focal point, and a light source directed at the focal point for directing light at the particles to generate fluorescence from the particles at or near the focal point. Opposing tubes result in opposing particle flows. The opposing particle flows act to reduce the velocity (or inertia) of the particles at the focal point, thereby increasing the residence time of the particles within the light produced by the light source. This acts to reduce the power requirements and increase the sensitivity of the detector compared to flow-through detectors without opposing flows.

Although specific embodiments have been illustrated and described herein, it will be appreciated by those of ordinary skill in the art that any arrangement that is calculated to achieve the same purpose may be substituted for the specific embodiments shown. Many adaptations of the invention will be apparent to those of ordinary skill in the art. Accordingly, this application is intended to cover any adaptations or variations of the invention. It is manifestly intended that this invention be limited only by the following claims and equivalents thereof.

What is claimed is:

1. A particle detector, comprising:
   a spherical/ellipsoid shell comprising spherical and ellipsoid mirrors that define a focal point within an interior of the shell;
   a pair of opposing first tubes passing through the spherical/ellipsoid shell and directed at the focal point, each of said tubes acting as inlets for directing particle flow in opposing directions to the focal point, wherein said tubes are substantially non-fluorescent; and
   a light source directed at the focal point for directing light at the particles to generate fluorescence from the particles at or near the focal point.

2. The particle detector of claim 1, wherein the light source is an ultra-violet light emitting diode or an ultra-violet laser.

3. The particle detector of claim 1, further comprising another pair of opposing tubes passing trough the spherical/ellipsoid shell and directed at the focal point.

4. The particle detector of claim 1, further comprising a photon counter located outside of the shell for receiving fluorescence photons from within the shell.

5. The particle detector of claim 4, further comprising an optical filter located between the shell and the photon counter.

6. The particle detector of claim 5, wherein said optical filter is capable of filtering scattered and reflected light from said light source.

7. The particle detector of claim 1, wherein the spherical mirror has a plurality of radial notches disposed therein for directing flows from the interior of the spherical/ellipsoid shell.

8. The particle detector of claim 1, wherein the light source is located within the spherical/ellipsoid shell or exteriorly of the spherical/ellipsoid shell.

9. The particle detector of claim 1, further comprising a light dump located opposite the light source and exteriorly of the spherical/ellipsoid shell, wherein said dump acts to prevent light from the light source from being reflected back into the spherical/ellipsoid shell after exiting the spherical/ellipsoid shell.

10. The particle detector of claim 1, wherein the interior of the spherical/ellipsoid shell is adapted for fluid flow coupling to an external pump.

11. The particle detector of claim 1, wherein exits of the respective tubes are located substantially equidistant from the focal point.

12. The particle detector of claim 1, wherein inside diameters of the respective tubes are substantially equal.

13. The particle detector of claim 1, wherein each of the pair of first tubes passes substantially concentrically through a respective one of a pair of second tubes to form a flow passage between an exterior of each first tube and an interior of the respective second tube, the flow passage for directing flows from the interior of the spherical/ellipsoid shell.

14. A particle detector, comprising:
   a body;
   first and second end caps disposed at opposite ends of the body;
   an ellipsoid mirror disposed within the first end cap;
   a spherical mirror disposed within the body so as to abut the ellipsoid mirror to form a spherical/ellipsoid cavity within the particle detector, the spherical and ellipsoid mirrors defining a focal point within the cavity;
   a pair of opposing tubes passing through the first end cap into the cavity and directed at the focal point, each of said tubes acting as an inlet for directing particles to the focal point in opposing directions, and wherein said tubes are substantially non-fluorescent;
   a light source directed at the focal point for directing ultra violet light at the particles;
   a photon counter disposed in the body between the second end cap and the spherical/ellipsoid cavity; and
   a filter disposed in the body between the photon counter and spherical/ellipsoid cavity.

15. The particle detector of claim 14, wherein the light source is a light emitting diode or a laser.

16. The particle detector of claim 14, further comprising another pair of opposing tubes passing through the first end cap into the cavity and directed at the focal point.

17. The particle detector of claim 14, wherein the light source is located within the spherical/ellipsoid cavity or exteriorly of the first end cap.

18. The particle detector of claim 14, further comprising a light dump connected to an exterior of the first end cap and located opposite the light source that acts to prevent light from the light source from being reflected back into the spherical/ellipsoid cavity after exiting the spherical/ellipsoid cavity.

19. The particle detector of claim 14, wherein the filter has a coating that acts to substantially prevent fluorescence therefrom.

20. A method for detecting particles, comprising:
directing a pair of opposing particle flows at a focal point within a spherical/ellipsoid cavity having an ellipsoid mirror and a spherical mirror;
directing ultra-violet light at the focal point to illuminate the particles at or near the focal point to generate fluorescence from the particles at or near the focal point; and
directing fluorescence generated at or near the focal point to a target point.

21. The method of claim 20, wherein directing fluorescence generated at or near the focal point to the target point comprises reflecting any fluorescence received at the ellipsoid mirror off of the ellipsoid mirror and onto the target point.

22. The method of claim 21, wherein directing fluorescence generated at the focal point to a target point further comprises reflecting any fluorescence received at the spherical mirror off of the spherical mirror, back to the focal point, and onto the ellipsoid mirror, and reflecting this fluorescence onto the target point.

23. The method of claim 20, further comprising directing another pair of opposing particle flows at the focal point.

24. The method of claim 20, wherein the ultra-violet light originates from within the spherical/ellipsoid cavity or exteriorly of the spherical/ellipsoid cavity.

25. The method of claim 20, further comprising directing the particle flow from the spherical/ellipsoid cavity through a plurality of notches in the spherical mirror.

26. The method of claim 20, further comprising filtering the fluorescence before the fluorescence arrives at the target point.

27. The method of claim 26, further comprising directing the filtered fluorescence to a photon counter.

28. The method of claim 20, wherein directing the pair of opposing particle flows at the focal point comprises substantially balancing the flows.

* * * * *